(12) United States Patent
Wetzel

(10) Patent No.: US 6,573,298 B2
(45) Date of Patent: Jun. 3, 2003

(54) METHOD FOR PROTECTING WOOD AND WOODEN ARTICLES FROM FUNGAL INFECTION

(75) Inventor: Ariane Wetzel, Frankfurt am Main (DE)

(73) Assignee: Nutrinova Nutrition Specialties & Food Ingredients GmbH, Frankfurt am Main (DE)

( * ) Notice: Subject to any disclaimer, the term of this patent is extended or adjusted under 35 U.S.C. 154(b) by 0 days.

(21) Appl. No.: 09/732,107

(22) Filed: Dec. 7, 2000

(65) Prior Publication Data

US 2001/0018454 A1 Aug. 30, 2001

(30) Foreign Application Priority Data

Jan. 25, 2000 (DE) .......................................... 100 03 170

(51) Int. Cl.$^7$ .......................... A01N 37/06; A01N 31/02
(52) U.S. Cl. ....................... 514/557; 514/560; 514/738; 504/157
(58) Field of Search ................................ 514/574, 557, 514/560, 738; 504/157

(56) References Cited

U.S. PATENT DOCUMENTS 4,585,795 A   4/1986   Linderborg ................ 514/558

FOREIGN PATENT DOCUMENTS

| DE | 297 01 633 U1 | 9/1997 |
| DE | 197 03 552 A1 | 8/1998 |
| JP | 10067607 | 3/1998 |
| JP | 10316511 | 12/1998 |
| WO | 96/11572 A1 | 4/1996 |

OTHER PUBLICATIONS

Derwent abstract no. 1998–447860, abstracting DE 19703552 (Aug. 1998).*

Derwent abstract no. 1997–386869, abstracting DE 29701633 (Jul. 1997).*

Chemical Abstracts 84:26867, abstracting DE 2513231 (Oct. 1975).*

Nikai Sueyoshi, Report No. 7 with German translation.

Holzforschung 17, 97 (1963).

Handbuch Lebensmittelzusatzstoffe (Food additives manual) section B11–1.2, P.3, 1997.

* cited by examiner

Primary Examiner—John Pak
(74) Attorney, Agent, or Firm—ProPat, L.L.C.

(57) ABSTRACT

The invention relates to wood which is impregnated with sorbic acid and/or one or more salts of sorbic acid. Furthermore, the invention relates to a method for protecting wood by treatment with sorbic acid and/or one or more salts of sorbic acid.

13 Claims, No Drawings

METHOD FOR PROTECTING WOOD AND WOODEN ARTICLES FROM FUNGAL INFECTION

The invention relates to wood which is impregnated with sorbic acid and/or one or more salts of sorbic acid. Furthermore, the invention relates to a method for protecting wood by treatment with sorbic acid and/or one or more salts of sorbic acid.

BACKGROUND OF THE INVENTION

Wood in a moist environment is susceptible to mold and other fungi. A great number of fungi are able to cause damage in wood. These include various wood-staining fungi which can grow relatively rapidly on fresh wooden surfaces and wooden surfaces exposed to weather. The stains which can be caused, for example by Aureobasidium pullulans, are frequently encountered in the case of untreated wood. They are known under the name "blue stains". The growth of such fungi can lead not only to impairment of the appearance of wood or articles made therefrom, but there is also the risk that fungi transfer from the wood to other articles or products and that even long-lasting forms of the molds can be given off into the ambient air. The inhalation of such fungi can, with sensitized persons, lead, for example, to asthma attacks.

To protect wood and wooden articles from fungal infection, a number of substances and methods of treatment have been proposed.

For example, wood may be protected by drying it to a low $H_2O$ content. The growth of fungi is bound to the presence of water, generally to water contents above 20%. If the dried wood is exposed to weather, at relatively high relative humidity, the effect of drying is soon eliminated again, however.

Paints, varnishes and similar coatings also prevent fungi from colonizing the surface of the wood or from penetrating into the wood. The methods are proven in practice, but some of them are labor-intensive or costly or only effective provided that wood or wooden articles do not pass into moist surroundings or the paints or coatings are not damaged. However, during transport and other mechanical stress, this is readily possible, so that the protective action is at least in part lost.

In addition, a large number of substances having fungicidal action are known which are used in practice as wood preservatives. For example, tar oils, organotin compounds, various chlorinated aromatic and aliphatic compounds and other substances which can be used alone or in combination. Many of these substances are distinguished by a pronounced activity against fungi. Their use is generally simple. The wood may be lastingly protected against fungal infection in many cases by impregnation. However, a disadvantage of these substances is that they are also distinguished by a greater or lesser toxicity which can make their use in sensitive areas a problem. This applies in particular to use in the food production sector, if transfer even of only traces to foods or food packaging cannot be reliably excluded. In particular in the case of odor-intensive wood preservatives such as the wood tar oils, there is also the risk that even traces of foods cause odor impairment. In practice, nevertheless, it is constantly being observed that especially wooden pallets on which raw materials are transported and delivered are infected during transport and storage by wood-decomposing fungi which can be carried into stores and production areas with the pallets and can thus develop to form a hygiene problem.

Some preservatives which are used to preserve various foods have already been tested for their applicability for preserving wood, especially in the form of derivatives which are not used as such for food preservation. The water-insoluble zinc salt of sorbic acid has, for example, been described as inactive (Holzforschung 17, 97 (1963)). Studies on the use of the commercially unavailable sodium sorbate on bamboo which, owing to its more solid structure, is not completely comparable with the conifer wood customarily used in Germany and which therefore should be somewhat more readily protected against fungal infection, generally resulted, even after a few days, in infection with fungi and worse results than the dehydroacetic acid tested as an alternative. Only at pH 3.0, which is not customary in practice, was sodium sorbate active in these studies (Hakko Kogaku Zasshi 37, 19 (1959)).

Food preservatives and their derivatives are not used in practice as wood preservatives, since they have hitherto been considered to be insufficiently active. In contrast to the wood preservatives used in industry, the preservatives used in food processing are harmless to health, however, so that the transfer of traces to food packaging would be somewhat more tolerable than with industrial preservatives. In addition, they are odor-neutral, so that no odor impairment of the foods is caused by them. This applies especially to sorbic acid, which is closely related structurally to the fatty acid present in food fats and is broken down in the same manner as the fatty acids in the metabolism of the body.

Surprisingly, it has now been found that sorbic acid and especially its water-soluble salts are thoroughly able to protect wood and wooden articles from wood-damaging fungi for a relatively long period even in moist surroundings. This protective action is also achieved at the higher pH of the wood, although in general reference is made to the fact that sorbic acid and its salts are only active at an acidic pH of the material to be preserved (for example: Handbuch Lebensmittelzusatzstoffe [Food additives manual], section B II-1.2, p. 3, 1997).

DESCRIPTION OF THE INVENTION

The invention therefore relates to wood which is impregnated with sorbic acid and/or one or more salts of sorbic acid.

In addition, the invention relates to a wood preservation method, which comprises treating wood with sorbic acid and/or one or more salts of sorbic acid.

For the purposes of the invention, salts of sorbic acid are in particular the water-soluble salts, preferably the sodium salt, potassium salt and magnesium salt.

The protective action of sorbic acid and its salts is of interest and important in particular for pallets for transporting raw materials for food manufacture. Such pallets are exposed during transport and storage to the most varied conditions, including in some circumstances the pallets themselves to high moisture, if the palleted material remains protected against moisture by an overwrap. Protecting the pallets against fungal infection is therefore not simple. However, it has been found that wood, after treatment with salts of sorbic acid, even in moist surroundings remains free from fungal infection for a relatively long time, in fact under conditions corresponding to more than normal circulation of the pallets. By this means wood and wooden articles, especially wooden pallets, which are to be used in the food production and food processing sector, may be protected against unwanted infection with molds without there being any risk that traces of conventional wood preservatives, which are harmful to health or have adverse odor, transfer to foods or food packaging.

Wood may be protected against fungi by a simple treatment with solutions of the salts of sorbic acid, without special or complex methods of application or impregnation being required which would go beyond the customary methods used in wood treatment. Suitable methods are all those by which the surface of the wood or the wood articles can be evenly wetted with solutions of sorbic acid and/or salts of sorbic acid, that is to say dipping, spraying, coating and other methods. The concentrations of sorbic acid and/or salts of sorbic acid are matched to the intended treatment method. They can be varied in principle within wide limits and are restricted upwards only by the solubility limit, and downwards by the low protective action at insufficient concentrations. Limited protective action can be achieved even at a few percent by weight, in particular if dry wood is used and uptake of the solutions is promoted by relatively long dipping times or the wood is intensively wetted by spraying or coating. Customarily, use is made of solutions of the salts in water, or alcohols, such as branched or unbranched $C_1$–$C_4$-alkanols and/or $C_2$–$C_4$-alkanediols or mixtures of these alcohols with water, in particular aqueous 1,2-propanediol having preferred concentrations in the range 1–50% by weight, in particular in the range 3–30% by weight, particularly preferably 10–40% by weight. Preference is given to solutions of the salts of sorbic acid in water, whereas for special conditions solutions in mixtures of water with volatile alcohols can be used for rapid drying or of less volatile alcohols for avoiding crack formation in the event of excessively rapid drying.

For particularly intensive protective action, instead of a simple dipping treatment, a pressure impregnation or impregnation after preceding evacuation can occur, in each case using solutions of sorbic acid and/or sorbic acid salts in water or mixtures of water and 1,2-propanediol.

After the treatment, generally simple drying in dry air is sufficient in order to achieve the desired protective action. Alternatively, obviously, also accelerated drying in heated rooms or chambers or in a warm or dry air stream is also possible.

The treatment is preferably performed on wooden parts destined for further processing, so that the entire surface comes uniformly into contact with the sorbic acid and/or the salts of sorbic acid. However, it can also be performed on finished wooden articles if the shape makes possible the contact of the entire surface with the solutions of sorbic acid and/or sorbic acid salts.

Surprisingly, the wood or wooden articles may be protected without disadvantageous activities having to be accepted. In particular, the wood and wooden articles remain practically odor-free. Although the color changes after the treatment to a brown color, this is thoroughly pleasing and somewhat more pleasant than, for example, untreated white wood or pinewood would be considered. The elasticity of the wood and its strength are not impaired by the treatment.

The invention is described by the following examples:

EXAMPLE 1

Immersion Impregnation with Aqueous Potassium Sorbate Solution Air-dry pine boards are dipped into a solution of 30% potassium sorbate in water for event, visible soaking of the surface. After the treatment they are air dried. The boards are then stored in the open and only protected against direct rainfall at usual room temperature together with untreated boards for three weeks. After completion of the storage the untreated boards have intensive blue stain infection, which covers virtually the entire surface, while the treated boards, despite storage directly next to the infected boards, remain free from fungal infection. Compared with fresh wood, there is only a staining to give a pale brown color.

EXAMPLE 2

Immersion Impregnation with a Solution of Potassium Sorbate in Aqueous 1,2-propanediol Air-dried pine boards are, as in example 1, dipped into a solution of 30% potassium sorbate in a mixture of 75% by volume of water and 25% by volume of 1,2-propanediol, further treated and stored. After completion of the storage, the boards are also completely free from fungal infection. Compared with example 1, the brown staining of the boards is somewhat more intense.

EXAMPLE 3

Spray Treatment with Aqueous Potassium Sorbate Solution

Air-dried pine boards are sprayed with a spraying pistol with a solution of 20% potassium sorbate in water until the surface is uniformly wet. The boards are then allowed to dry and are stored as in example 1. After completion of the storage the result corresponds to that of example 1.

EXAMPLE 4

Storage at High Atmospheric Humidity

Two pinewood boards in each case are dipped into potassium sorbate solution (see table 1 for concentrations) and stored in a saturated water vapor atmosphere at 35° C. In parallel with this, in each case two pinewood boards, after the dipping, were additionally dirtied with soil on the surface in order to achieve greater surface contamination with molds. The boards were individually packed in film in order to exclude cross contaminations and regularly visually examined for fungal infection. The results are shown in table 1.

TABLE 1

| | Dwell time in potassium sorbate solution min | Concentration of potassium sorbate solution % by weight | With soil | Fungal infection |
|---|---|---|---|---|
| K1 | — | — | — | yes/from day 29 marked/from day 53 |
| V1 | 10 | 1 | no | no/after 81 days |
| V2 | 10 | 2 | no | no/after 81 days |
| V3 | 10 | 5 | no | no/after 81 days |
| V4 | 5 | 10 | no | no/after 81 days |
| K2 | — | — | yes | yes/from day 29, increasing with storage |
| V5 | 10 | 1 | yes | little/from day 43 |
| V6 | 10 | 2 | yes | little/from day 53 |
| V7 | 10 | 5 | yes | no/after 81 days |
| V8 | 5 | 10 | yes | no/after 81 days |

What is claimed is:

1. A wood pallet impregnated with a solution comprising (i) a solvent selected from the group consisting of $C_{2-4}$ alkane idol and a mixture of water and $C_{2-4}$ alkane diol, and (ii), sorbic acid or one or more salts of sorbic acid or a combination of sorbic acid and one or more salts of sorbic acid, which solution does not contain tar oils, organotin compounds, chlorinated aromatic compounds or chlorinated aliphatic compounds.

2. The wood pallet as claimed in claim 1, wherein the salt of sorbic acid is selected from the group: sodium salt, potassium salt, magnesium salt and mixtures of these salts.

3. The wood pallet as claimed is claim 2, wherein the salt is potassium sorbate.

4. The wood pallet as claimed in claim 1, wherein the sorbic acid or one or more salts of sorbic acid or the combination of sorbic acid and one or more salt of sorbic acid are used in a treatment solution at a concentration of 1–50% by weight.

5. The wood pallet as claimed in claim 4, wherein the sorbic acid or one or more salts of sorbic acid or the combination of sorbic acid and one or more salts of sorbic acid are used in the treatment solution in concentrations of 3–30% by weight.

6. A method for protecting wood against fungal infections in moist surroundings comprising treating wood with a solution comprising (i) a solvent selected from the group consisting of $C_{2-4}$ alkane diol and a mixture of water and $C_{2-4}$ alkane diol, and (ii) sorbic acid or one or more salts of sorbic acid or a combination of sorbic acid and one or more salts of sorbic acid, which solution does not contain tar oils, organotin compounds, chlorinated aromatic compounds or chlorinated aliphatic compounds.

7. The method as claimed in claim 6, wherein the $C_{2-4}$ alkanediol is 1,2-propanediol.

8. The method as claimed in claim 6, wherein the sorbic acid or one or more salts of sorbic acid or the combination of sorbic acid and one or more salts of sorbic acid are used in the treatment solution in concentrations of 1–50% by weight.

9. The method as claimed in claim 8, wherein the sorbic acid or one or more salts of sorbic acid or the combination of sorbic acid and one or more salts of sorbic acid are used in the treatment solution in concentrations of 3–30% by weight.

10. The method as claimed in claim 6, wherein the treatment is performed in the form of an immersion impregnation.

11. The method as claimed in claim 6, wherein the treatment is performed at elevated pressure.

12. The method as claimed in claim 6, wherein the wood, prior to the treatment, is exposed to reduced pressure.

13. The method as claimed in claim 6, wherein the solution of sorbic acid or one or more salts of sorbic acid or the combination of sorbic acid and one or more salts of sorbic acid are applied to the surface of the wood by spraying or coating.

* * * * *